(12) United States Patent
Lihl et al.

(10) Patent No.: US 9,097,632 B2
(45) Date of Patent: Aug. 4, 2015

(54) DEVICE FOR THE LIGHT STIMULATION AND CRYOPRESERVATION OF BIOLOGICAL SAMPLES

(71) Applicant: Leica Mikrosysteme GmbH, Vienna (AT)

(72) Inventors: Reinhard Lihl, Vienna (AT); Rainer Wogritsch, Vienna (AT); Heinz Plank, Wiener Neudorf (AT)

(73) Assignee: LEICA MIKROSYSTEME GMBH, Vienna (AT)

( * ) Notice: Subject to any disclaimer, the term of this patent is extended or adjusted under 35 U.S.C. 154(b) by 0 days.

(21) Appl. No.: 13/778,720

(22) Filed: Feb. 27, 2013

(65) Prior Publication Data
US 2013/0227970 A1 Sep. 5, 2013

(30) Foreign Application Priority Data

Mar. 2, 2012 (AT) .............................. A 50051/2012

(51) Int. Cl.
*F25D 25/00* (2006.01)
*F25B 19/00* (2006.01)
(Continued)

(52) U.S. Cl.
CPC ............... *G01N 1/42* (2013.01); *B29C 45/0053* (2013.01); *B29C 2045/0075* (2013.01); *B29K 2083/005* (2013.01); *G01Q 30/10* (2013.01); *G02B 7/007* (2013.01); *G21K 7/00* (2013.01)

(58) Field of Classification Search
CPC ........... G02B 7/007; G01N 1/42; G01N 1/44; G01N 2021/1731; G01Q 30/10; G21K 5/08; G21K 7/00
USPC ....................................... 62/51.1, 264, 62, 78
See application file for complete search history.

(56) References Cited

U.S. PATENT DOCUMENTS

| 4,942,134 A | * | 7/1990 | Winefordner et al. ........ 436/161 |
| 5,230,219 A | * | 7/1993 | Ichikawa et al. .................. 62/78 |

(Continued)

FOREIGN PATENT DOCUMENTS

| AT | 398432 | 12/1994 |
| DE | 3443906 | 6/1986 |

(Continued)

OTHER PUBLICATIONS

E Kovács, Á Keresztes, Effect of gamma and UV-B/C radiation on plant cells, Micron, vol. 33, Issue 2, 2002, pp. 199-210, ISSN 0968-4328, http://dx.doi.org/10.1016/S0968-4328(01)00012-9. (http://www.sciencedirect.com/science/article/pii/S0968432801000129) Keywords: Plant cell; UV-B/C; Gamma irradiation; Ozone; Plastid; Cell wall.*

(Continued)

*Primary Examiner* — Frantz Jules
*Assistant Examiner* — Steve Tanenbaum
(74) *Attorney, Agent, or Firm* — Hodgson Russ LLP (57) ABSTRACT

In a device (1) for rapid pressure-freezing an aqueous sample (3), such as a biological specimen, a pressurized cooling medium can be fed into a high-pressure chamber (11) into which a sample holder (30) containing a sample (3) is inserted and which is sealed with a pressure-tight seal, to the location of the sample holder (30) held therein. The high-pressure chamber (11) comprises a viewing window structure (2) with a pressure-tight window (20), through which light can be directed from the outside onto the sample (3) located in the sample holder (30). The window (20) can comprise a transparent window element made of a high-pressure-resistant material, wherein the window element (20) is held by a pressure- and temperature-resistant window bearing provided in the high-pressure chamber.

8 Claims, 4 Drawing Sheets

(51) Int. Cl.
  *F25D 23/00* (2006.01)
  *F24F 3/16* (2006.01)
  *G01N 1/42* (2006.01)
  *B29C 45/00* (2006.01)
  *G01Q 30/10* (2010.01)
  *G02B 7/00* (2006.01)
  *G21K 7/00* (2006.01)
  *B29K 83/00* (2006.01)

(56) References Cited

U.S. PATENT DOCUMENTS

| | | | |
|---|---|---|---|
| 5,237,825 A | | 8/1993 | Menzi et al. |
| 5,257,128 A | * | 10/1993 | Diller et al. ............ 359/395 |
| 5,493,865 A | * | 2/1996 | Wohlwend ............ 62/51.1 |
| 5,598,888 A | * | 2/1997 | Sullivan et al. ............ 165/263 |
| 7,632,469 B2 | * | 12/2009 | Bierleutgeb ............ 422/536 |
| 7,824,902 B2 | * | 11/2010 | Selker et al. ............ 435/288.7 |
| 7,883,864 B2 | * | 2/2011 | Fujisato et al. ............ 435/40.5 |
| 2003/0137724 A1 | * | 7/2003 | Tonooka ............ 359/385 |
| 2007/0227719 A1 | * | 10/2007 | Voelker ............ 165/256 |
| 2007/0231787 A1 | * | 10/2007 | Voelker ............ 435/4 |
| 2010/0184012 A1 | * | 7/2010 | Voelker ............ 435/2 |

FOREIGN PATENT DOCUMENTS

DE   10025512   1/2001
EP   0853238   7/1998

OTHER PUBLICATIONS

McCurdy DW, Pratt LH, Immunogold electron microscopy of phytochrome in Avena: identification of intracellular sites responsible for phytochrome sequestering and enhanced pelletability, J Cell Biol., J Cell Biol., vol. 103, 1986, pp. 2541-2550, (http://www.ncbi.nlm.nih.gov/pubmed/3536968).*

Hisada, Et al, Technical Advance: An Automated Device for Cryofixation of Specimens of Electron Microscopy using Liquid Helium, Plant Cell Physiol, vol. 42, Issue 9, 2001, pp. 885-893, http://dx.doi.org/doi:10.1093/pcp/pce132, (http://pcp.oxfordjournals.org/content/42/9/885.full.pdf+html).*

Leica EM HPM100 Operating Manua, Dec. 2010, Leica Mikrosysteme GmbH, Hernalser Hauptstrasse 219, 1170 Vienna, Austria, Version 167120032, 35-39.*

Thomas H. Jackson, Aydin Ungan, John K. Critser, Dayong Gao, Novel Microwave Technology for Cryopreservation of Biomaterials by Suppression of Apparent Ice Formation, Cryobiology, vol. 34, Issue 4, Jun. 1997, pp. 363-372, ISSN 0011-2240, http://dx.doi.org/10.1006/cryo.1997.2016. (http://www.sciencedirect.com/science/article/pii/SO0112240979201.*

* cited by examiner

DEVICE FOR THE LIGHT STIMULATION AND CRYOPRESERVATION OF BIOLOGICAL SAMPLES

CROSS REFERENCE TO RELATED APPLICATIONS

This application claims priority of the Austrian patent application number A50051/2012 filed Mar. 2, 2012, the entire disclosure of which is incorporated by reference herein.

FIELD OF THE INVENTION

The invention relates to a device for rapidly freezing an aqueous sample, in particular a biological sample, under pressure, specifically using a high-pressure chamber into which a sample holder containing the sample can be inserted, and which can be sealed forming a pressure tight seal, wherein a cooling medium can be supplied to the high pressure chamber and fed to the site of the sample holder located therein. The invention further relates to a method of high-pressure freezing that is suitable for the device.

BACKGROUND OF THE INVENTION

A high-pressure freezing device of the above-stated type is described in DE 100 25 512 A1, in which additionally a particularly rapid pressure increase is achieved using a pre-stressed pneumatic cylinder.

A device produced by the applicant for the high-pressure freezing of biological and industrial samples is currently being successfully marketed under the name "Leica EM HPM100". With the "Leica EM HPM100", samples can be cooled to low temperatures, such as below −100° C., within only a few ms using liquid nitrogen under a pressure of up to 2100 bar (cryopreservation). In this case, sample have a thickness of up to 200 μm and are vitrified during cryopreservation as a result of the rapid cooling process, i.e., the formation of crystalline ice is largely prevented, since crystallization could deteriorate or even destroy the microstructure of the sample.

In the "Leica EM HPM100", a sample cartridge is used for holding the sample under high pressure conditions during the freezing process. The sample cartridge is made of high-strength plastic and comprises three components, specifically two semicylinders with a channel, which can be used to conduct cooling fluid, and a support plate having an opening designed to receive the sample. The pressure at the location of the sample is generated by the cooling fluid, which is brought to a pressure of 2100 bar for this purpose.

Figure 8:
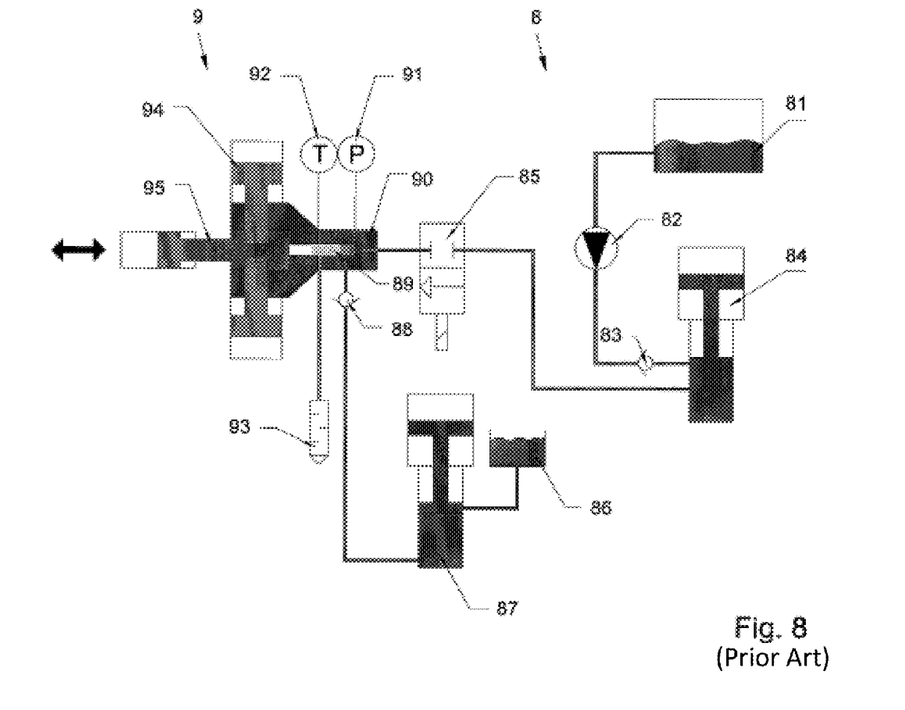
FIG. 8 is a schematic depiction of the high-pressure freezing system according to the prior art.

FIG. 8 shows the principal structure of the high-pressure freezing system 9, which is based upon the "Leica EM HPM100" and can also be used for freezing systems according to the invention. The sample cartridge 89 is introduced into the high-pressure chamber 90 by means of a loading device 95. The high-pressure chamber 90 is sealed for the freezing process by locking the loading device 95 with locking pins 94. The freezing process is implemented by introducing pressurized liquid nitrogen (LN2), which is fed rapidly into the space inside the cartridge 89. For this purpose, the system 9 is equipped with a supply 8 of a cooling medium. In the cooling medium supply 8, LN2 is conducted from a cooling medium tank 81 via a cooling medium pump 82, downstream of which a flow check valve 83 is located, to a pressure intensifier 84 operated with compressed air. Here, the cooling medium LN2 that is used is brought to a target pressure of, e.g., 2100 bar. The outlet of the pressure intensifier 84 is connected to the high-pressure chamber 90 by a supply line via a high-pressure valve 85. The high-pressure valve 85 is designed to rapidly supply pressurized LN2 to the interior of the high-pressure chamber 90 when opened, so that the sample held in the cartridge 89 is high-pressure frozen within a very short time interval. A pressure sensor 91 and a temperature sensor 92 monitor the freezing process. Pressure in the chamber 90 can be released via an outlet opening 93 (outlet with noise damper), to allow the cryopreserved sample to be removed.

The high-pressure chamber also offers the option of supplying an additional liquid ("fill liquid"), e.g., an alcohol (particularly ethanol), wherein said fill liquid is supplied to the high-pressure chamber 90 from a tank 86 via a pump/metering system 87, downstream of which a flow check valve 88 is located. In some applications the alcohol can be used to fill the chamber prior to the freezing process, for example; when the freezing process starts, LN2 displaces the alcohol. In many cases, use of the alcohol offers the advantage of a faster build-up of pressure when the LN2 is fed in. However, use of the fill liquid is not mandatory, especially since various types of samples should not come into contact with alcohol. With the apparatus described here, good cooling results can be achieved even without the use of a fill liquid such as alcohol, in particular.

For specific areas of research and development, it is worthwhile to analyze the behavior of a sample following stimulation with light, particularly from the visible region, particularly by analyzing the state achieved through photostimulation. Analyses of this type are conducted, for example, on biological specimens such as plant cells and cyanobacteria. However, under normal conditions (i.e., under the normal living conditions of the biological parent material, generally at ambient temperature and pressure) the photostimulated state is short-lived, and therefore, additional measures are required to fix the transient stimulated state of the sample. The cryopreservation described in the introductory part is suitable for this purpose; rapidly freezing the sample under high pressure is desirable because it allows biological samples to be vitrified without the formation of ice crystals. With known high-pressure freezing devices, however, irradiation of the sample is possible only outside of the high-pressure chamber, since the interior of the high-pressure chamber is inaccessible or inadequately accessible to light. However, since the process for loading a sample into the high-pressure chamber takes several seconds and is difficult to shorten due to limitations of the equipment, the amount of time required to load a sample is far greater than the lifespan of the light-stimulated state to be analyzed, which is why with known devices it is difficult to impossible to implement cryopreservation fast enough following optical stimulation of the sample.

SUMMARY OF THE INVENTION

"High pressure" is understood in this disclosure as relating to a pressure range that will result in a marked decrease (i.e., by several ° C.) in the melting point of water. According to its phase diagram, the maximum possible decrease in the melting point of pure water occurs at 2045 bar, at which pressure level it is lowered to −22° C. However, pressures smaller than this value of 2045 bar are generally sufficient, especially since pure water is, of course, never present in biological samples. In experiments conducted by the inventors, good cryopreservation results were achieved at pressure levels of less than 2000 bar, specifically at approx. 1600 bar. Therefore, the pressure ranges in consideration here are several hundred bar, preferably between 1000 and 2200 bar.

Thus, the invention addresses the problem of providing a high-pressure freezing device enabling the light stimulation of samples by an intense light pulse, followed immediately by cryopreservation of the stimulated samples, in a simple manner. In this context, it is desired that the interval of time between stimulation and the freezing process and the conditions of stimulation are reproducibly adjustable to the greatest extent possible.

This problem is solved by a device of the type described in the introductory part wherein, according to the invention, the high-pressure chamber has a viewing window structure having a pressure-tight window, through which light is supplied from the outside and can be directed toward or shined onto the sample located in the sample holder.

The invention is based upon the insight that the desired short period of time between photostimulation and freezing under high-pressure conditions can be achieved by light-stimulating the sample which has been loaded into the high-pressure chamber. In this way, it is possible to preserve the light-stimulated state sufficiently rapidly, without having to take undesirable delays into account. The invention therefore enables analysis of the photostimulated sample, for example, in a electron cryo-microscope, wherein the actual analysis can optionally be preceded by additional preparation steps, such as thin cutting in a cryo-ultramicrotome.

In one particularly advantageous development of the invention, the window is embodied as comprising a window element made of a material resistant to high pressure, which is at least partially transparent (in particular in those areas through which the light enters) to the light that is supplied to the high-pressure chamber from the outside, wherein the window element is held by a pressure-resistant and temperature-resistant window bearing provided in the high-pressure chamber.

Further it may be advantageous when the high-pressure chamber is provided with a sample holder made of a material which is transparent to the light supplied to the high-pressure chamber from the outside. In this case, the sample holder (sample cartridge) may have a sample carrier and at least one transparent shell piece, wherein the sample carrier has an opening for receiving the sample. Moreover, the at least one shell piece may be provided with a channel for a cooling medium, wherein the sample carrier is enclosed in the mounted sample holder by the at least one shell piece, and the channel of the at least one shell piece leads from an external orifice to the area of the opening in the sample carrier. This allows the sample to be photostimulated and then cryopreserved in the same position in the sample holder, thereby facilitating the reliable preservation of the photostimulated state. Placing the sample in the sample cartridge keeps it stable in position throughout the entire stimulation/preservation process; also, the sample cartridge forms a "chamber within a chamber", which conducts the cooling medium in a targeted manner to the location of the sample, thereby ensuring a rapid cooling process.

More particularly, the pressure-tight window allows light to be radiated in directly from a suitable light source at the required light intensity. Alternatively, it is possible to insert a light guide, e.g. realized as a glass fiber cable, from the outside to the viewing window, with the end of the light guide being pressed against the viewing window. This will allow light at a selectable wavelength and/or intensity and/or pulse length to be conducted via the light guide to the sample. For this purpose, the viewing window structure may advantageously have an opening that serves as a light passage, the axis of which is aligned with the location of the sample, and in which a light guide that can be connected to the light source can be moved up to the window.

To ensure a temporally fixed sequence of the stimulation/preservation process, a control unit designed for controlling the light source for the light to be supplied to the sample may conveniently be associated with the device, wherein an output of a sensor or a switching means of the cooling medium circuit may be connected to the control unit, and the light source can be actuated at an adjustable time interval from the trigger signal for the sensor.

A further aspect of the invention relates to a method for rapidly freezing an aqueous sample, in particular a biological specimen, in a high-pressure chamber, wherein the method comprises the following steps:
 irradiating the sample with light through a pressure-tight window in the high-pressure chamber,
 exposing the sample to a cryogenic liquid—such as liquid nitrogen—under pressure (particularly under high-pressure conditions),
wherein light is radiated in according to a definable time correlation based upon a signal for activating the exposure of the sample to cryogenic liquid.

In this case, where the sample is held in a sample holder which is transparent (at least at those areas through which light will pass) to the light used during irradiation, it will be advantageous if the sample holder holding the sample is placed in the high-pressure chamber and locked in place. Further, the activation signal may be derived from a switching means for exposing the sample to the cryogenic liquid, or from a switching signal relating to said switching means, wherein the signal thus derived can then be used as a trigger signal for irradiating the sample, optionally taking into account an adjustable time delay.

BRIEF DESCRIPTION OF THE DRAWING VIEWS

In what follows, the invention and pertinent preferred implementations and further developments will be explained in detail based on an exemplary, non-limiting embodiment, which is illustrated in the attached set of drawings. The drawings show.

DETAILED DESCRIPTION OF THE INVENTION

The exemplary embodiment relates to a high-pressure freezing system, which is based upon the layout of the "Leica EM HPM100" and represents a development thereof. The principal structure of the high-pressure freezing system, which was described above in reference to FIG. 8, is also used in the device of the exemplary embodiment. It should be emphasized, however, that the invention is not limited to this exemplary embodiment or to high-pressure freezing systems such as those based upon the stated Leica device, but also includes other implementations of the stimulation/preservation process based on the inventive concept as defined in the claims.

Figure 1:
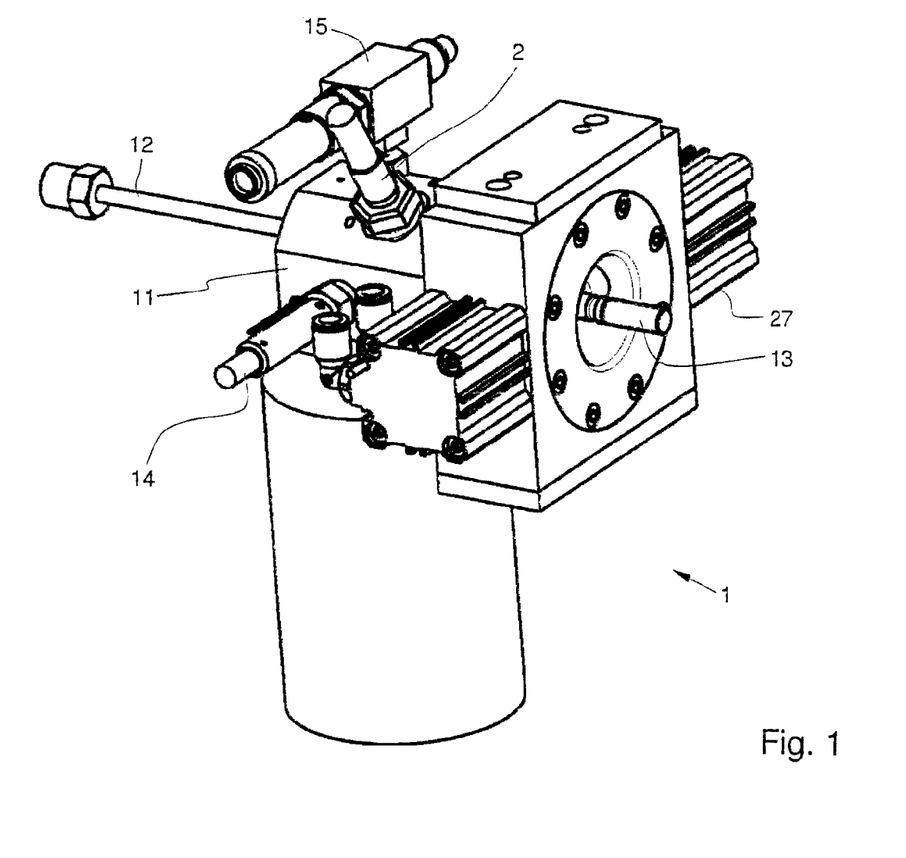
FIG. 1 is a perspective view of the high-pressure freezing system according to the exemplary embodiment.
Figure 2:
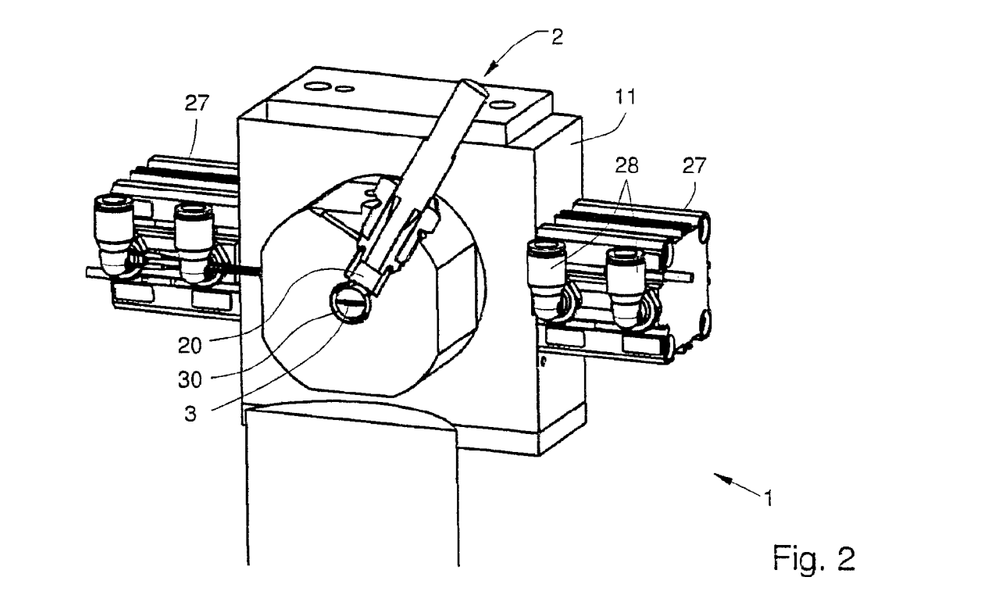
FIG. 2 is a sectional view of the system of FIG. 1, and particularly of the viewing window therein.
Figure 4:
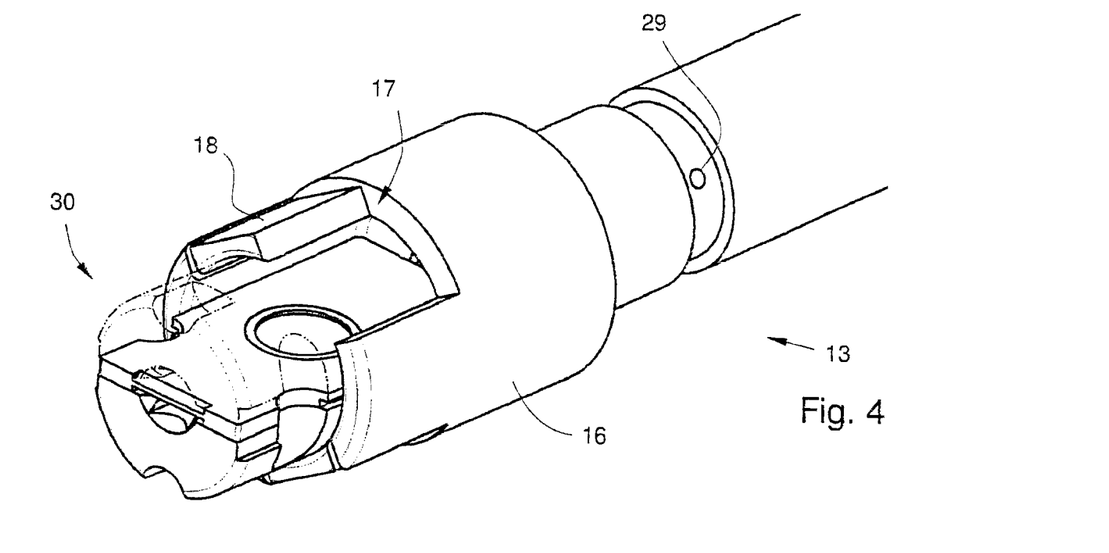
FIG. 4 is a perspective view of the sample cartridge.

FIG. 1 shows the entire high-pressure freezing system 1 according to the exemplary embodiment, in a perspective view. A high-pressure chamber 11 of the known type has a high-pressure line 12 for a cryogen, in this case liquid nitrogen (LN2), and a holder 13 for a cartridge (FIGS. 2 and 4). As is already known from the "Leica EM HPM100", the holder 13 is inserted with the sample cartridge into the chamber 11 and is fixed in place, wherein the space inside the chamber is tightly sealed by means of gaskets (not shown) on the holder. The longitudinal axis of the chamber, along which the holder is inserted, extends horizontally. FIG. 1 also shows a sensor 14, which is attached to the chamber 11, for measuring the temperature in the interior of the chamber; opposite to the sensor 14 there is a sensor (not shown in FIG. 1) for measuring the pressure level inside the chamber. Additionally, the alcohol supply with a flow check valve is indicated by the reference sign 15.

FIG. 1 also shows the housings 27 for the locking devices on both sides of the chamber 11. The housings 27 house the locking pins 94 (FIG. 8) described in the introductory part and the pneumatic cylinders that actuate said pins, the air supply connections 28 of which are shown in FIGS. 1 and 2. The locking pins and/or pneumatic cylinders are monitored by a sensor (not shown in FIG. 2; element 71b in FIG. 7), the signal from which serves to confirm successful locking. This ensures that the freezing process can be implemented only when the chamber is locked. For this purpose the piston of one of the pneumatic cylinders may, for example, be equipped with a magnet, which activates a reed contact of the sensor 71b when the piston is actuated. Such a sensor with a reed contact can be easily attached and positioned in a suitable position on the exterior of the housing 27 of the pneumatic cylinder (e.g., in an outer groove). In the embodiment shown, a fixed timing sequence is set, in which the signal from the sensor 71b confirming successful locking starts the freezing process, optionally following a system-induced and/or additionally adjustable delay.

According to the invention (and in contrast to the "Leica EM HPM100"), the high-pressure chamber 11 is equipped with a viewing window structure 2, which allows the sample placed in the chamber 11 to be irradiated at this very location with light radiated in from the outside, e.g., with white light or blue light (at a maximum wavelength of 460 nm).

Figure 3:
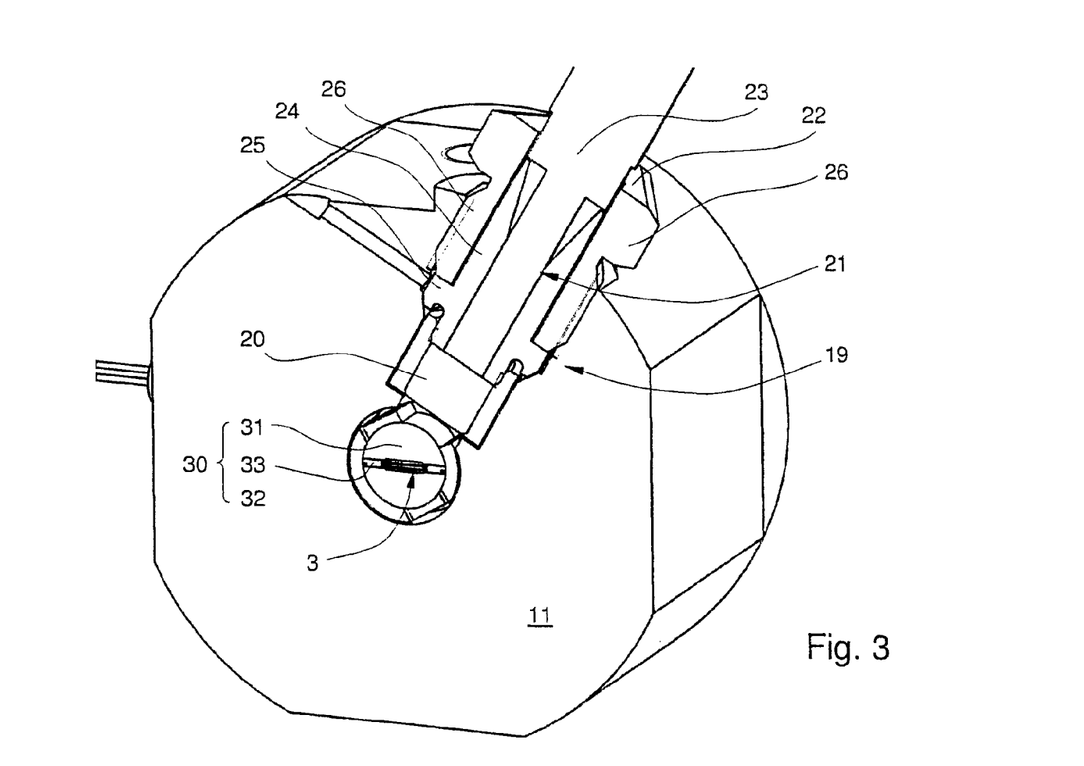
FIG. 3 is an enlarged section of the sectional view of FIG. 2.

The sectional views of FIGS. 2 and 3 illustrate the viewing window structure 2. The sectional plane is vertical, extending through the center axis of the viewing window and perpendicular to the longitudinal axis of the chamber. The viewing window structure 2 is held in a window opening 19 in the chamber 11 and is fixed in place by a threaded connection. A viewing window 20 is held by an insert 22, which has a tubular basic shape with a central opening 21, the axis of which coincides with the center axis of the window 20. The insert 22, together with the window opening 19, forms a window bearing for the window 20.

The opening 21, which extends along the axis of the insert and serves as a light passage, accommodates one end of a light guide 23, which preferably butts up against the window 20. The axis of the light passage, which thus determines the direction in which the light shines through the light guide 23, is directed toward the sample 3 held in the cartridge 30, and may be perpendicular to the longitudinal axis of the chamber 11, as shown in this exemplary embodiment.

The insert 22 comprises a window holder 24, which in turn has a shoulder 25 on the outside of the tubular basic shape, and a retaining screw 26 that interacts with said shoulder. The retaining screw is screwed into a female thread of the opening in the chamber and presses against the shoulder 25, ensuring a pressure-tight attachment of the window 20.

As a viewing window 20, for instance a so-called viewing cell may be used, such as the Sitec 740.01 viewing cell (Sitec-Sieber Engineering AG, Aschbach, Switzerland), which has a colorless sapphire as the window element. Viewing cells of this kind satisfy the requirements of the invention with respect to tightness and pressure and temperature resistance of the viewing window, with a width of optical view of 6 to 28 mm.

Alternatively, a block of transparent industrial diamond may be used as a viewing window. For example, the diamond block may be soldered to a pressure-tight threaded connection; for this, the diamond material can be brazed under a vacuum, which will produce a reliable connection. Such a unit comprising a screw connection and diamond block can be used as a viewing window 20 according to the invention. In place of a transparent diamond, any high-strength material can be used that will satisfy the requirements with respect to pressure tightness and transparency in the light region that is used, such as diamond, sapphire, etc.

It should be noted that, in contrast to the viewing window 20 and the light passage 21, the remaining structure of the chamber 11 is light impermeable, since it is constituted by components made of steel or aluminum, for example, and any plastic parts that may be used (e.g., seals) will be made of light impermeable plastic or rubber as well. This prevents any undesirable influence on the sample from disruptive light following photostimulation.

Figure 5:
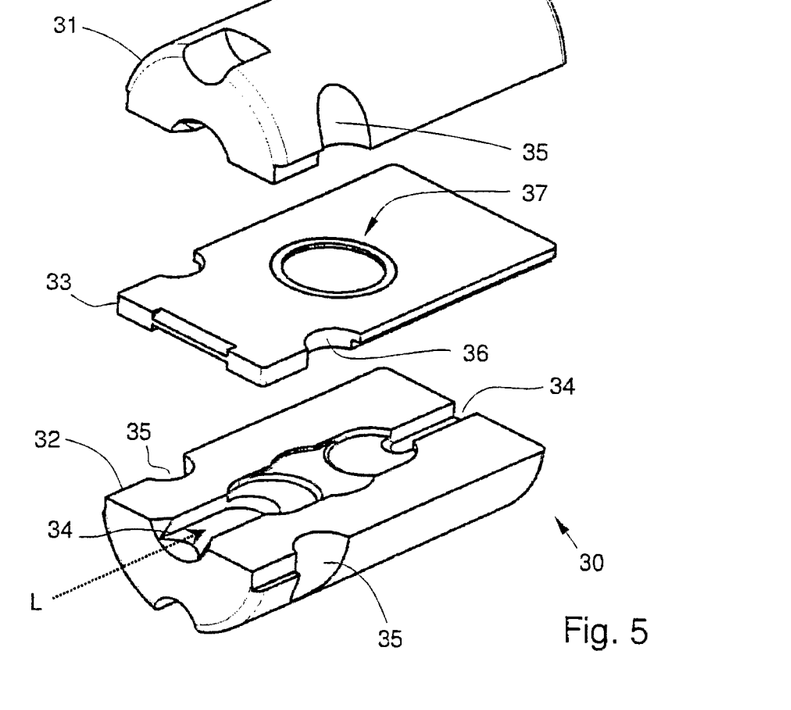
FIG. 5 is an exploded view of the sample cartridge of FIG. 4.

FIG. 4 shows the sample cartridge 30, which is held in the end piece 16 of the holder 13. FIG. 5 shows an exploded view of the cartridge 30. The end piece 16 is made of high-grade steel, for example; it is configured in the shape of a cup (the cup being oriented parallel to the longitudinal axis, and therefore horizontally in the exemplary embodiment) and has a recess 17 on the side that corresponds to the location of the viewing window 20. The end piece 16 comprises two opposing insert pieces 18 (also made of steel) with a plano-concave shape. The insert pieces 18 serve as flexible tongues and impart a spring effect for holding the parts of the sample cartridge together. To make space for the viewing window, the insert parts 18 are offset to each other; in other embodiments, these elements can be attached in a vertical direction.

The cartridge 30 comprises a cover piece 31 and a base piece 32. A support plate 33 is positioned between the pieces 31, 32 of the cartridge. In FIG. 4 the cover piece 31 is indicated only by dotted-dashed lines, in order to improve visibility of the support plate 33. The cover piece 31 and the base piece 32 have a basic shape which is substantially semicylindrical, wherein on the flat inner surface of the base piece 32, and optionally also on the flat inner surface of the cover piece 31, a channel 34 is provided, extending in the longitudinal direction, and allowing that a cooling medium can be conducted to the sample therethrough. This allows LN2 to flow from both sides to the sample 3, so as to promote rapid cooling. In the embodiment shown, to further improve the supply of LN2, a channel 34 is provided from each of the two end faces. This allows the LN2 to flow through the cartridge 30, more specifically substantially along the longitudinal axis of the cartridge, in the direction of the dotted arrow L in FIG. 5. In the holder 13 (inside the cup, near or in the "base surface" thereof), an opening is provided, which leads above an outlet opening 29 located outside of the chamber 11, and therefore serves as an outlet 93 for gases or liquids (including an all-purpose fill liquid such as ethanol) that are displaced by the LN2. This outlet path to the opening 29 is dimensioned so as to allow that a certain quantity of LN2 (0.25 L) can flow through the cartridge, while this does not result in a decrease in pressure within the time that is required for cryopreservation (approximately 300 to 500 ms); the chamber fill escapes through the outlet opening 29 as a result of a release of the pressure inside the chamber 11. If such an opening for the exit of displaced fluids were not present, it would be possible to achieve the desired pressure by means of a rapid supply of LN2, but not be a rapid cooling.

In the pieces 31 and 32 of the cartridge, lateral notches 35 may be provided arranged opposite to each another in pairs, for example, for blocking the cartridge against movement in the longitudinal direction and/or fixing the components in relation to one another.

The components 31, 33 of the cartridge 30 are made of a transparent plastic, such as polycarbonate or polystyrene. At least the cover piece 31 is made of a transparent material; in the interest of facilitating handling (and also to account for the possibility of confusion), it is sensible if the base piece 33 is also made of a transparent material. The support plate 33 is made, e.g., of PEEK (polyetherether ketone), which facilitates processing. These materials have a high stability in terms of pressure resistance and low-temperature behavior over the pressure and temperature ranges used, and at the same time are sufficiently transparent in the light region used for optical stimulation, in this case for wavelengths >400 nm. The semicircular shape is also advantageous in terms of optics, since the light can be focused onto the sample.

Figure 6:
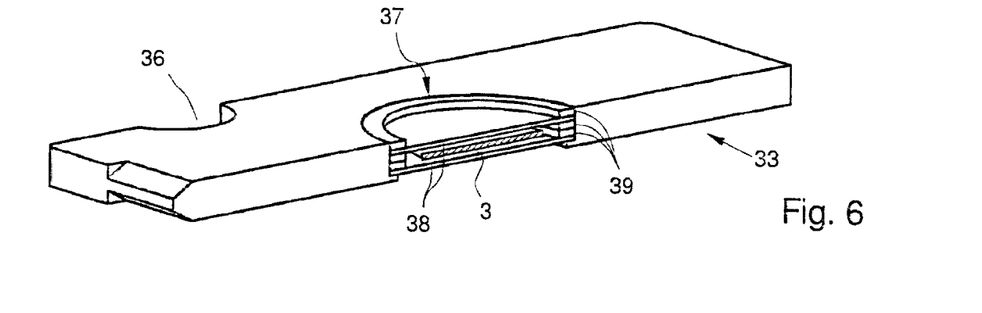
FIG. 6 is a longitudinal section of the support plate for the sample, from a perspective view.

FIG. 6 shows a longitudinal section of the support plate 33 along a vertical plane, in which the space designed to accommodate a sample 3 is shown opened in a sectional view. The support plate 33 has a notch 36 on each side, with each notch corresponding to one of the notches 35 in the cover and base pieces 31, 32, and having at its center a circular opening 37, in which the sample 3 is held between two disks 38 made of sapphire, for example. The distance between the disks can be adjusted using spacer rings 39. The sapphire disks 38 also serve to protect the sample 3, since otherwise the rapid flow of LN2 required for cooling would carry the sample along with it. The sapphire disks 38 are, e.g., 110 µm thick, with a diameter of the opening 36 being 6 mm. In one variant that has an opening that is 3 mm in diameter, a smaller disk thickness of 50 µm can be sufficient. The material sapphire is preferred here, because it is characterized by high stability and provides a good substrate for cell cultures and bacteria. Moreover, sapphire has the added advantage of high thermal conductivity, which ensures rapid cooling of the sample.

The entire cartridge 30 is dimensioned such that, within a period of preferably 500 ms, the necessary pressure (e.g., 2000 bar=200 MPa) can be built up and held, wherein within the same amount of time a rapid freezing of the sample 3 can be achieved.

Figure 7:
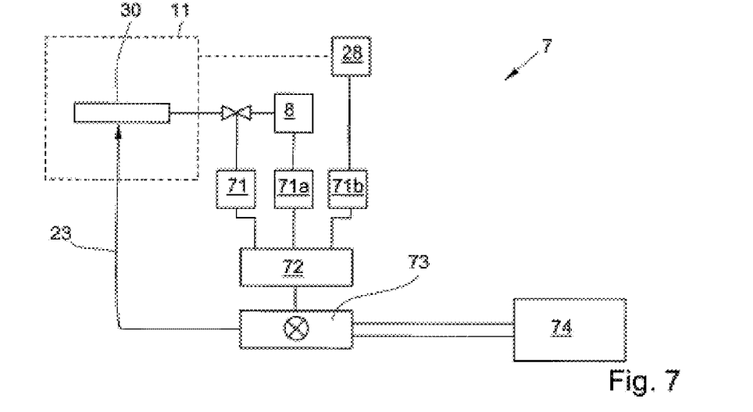
FIG. 7 is a block diagram illustrating the control of light stimulation.

FIG. 7 shows a block diagram of the trigger control system 7 for light stimulation, which enables controlling of the light pulse for stimulation and of the freezing process with regard to time, optionally by computer control. The intake valve for the LN2 is monitored by a sensor 71, e.g. realized as a reed contact. The sensor is activated, for example, when the intake valve is opened to start the build-up of pressure and the cooling process, and triggers the light stimulation of the sample. The actual pressure/cooling process begins a certain amount of time after the opening of the intake valve; this time interval can be determined in advance (e.g., using measurements taken by the temperature sensor based upon oscilloscope monitoring;

for this purpose, the temperature sensor must have a corresponding resolution per time unit), and in the case shown here, amounts to approximately 30 ms, for example. The start of light stimulation is triggered directly by the sensor signal, therefore resulting in an irradiation time that corresponds to the stated period of time, in this case 30 ms.

With another sensor 71a, which is connected to another switching component of the cooling system 8, a different amount of time for irradiation prior to freezing can be implemented. In the embodiment shown, the activation of the locking pins 94 (more precisely: the signal confirming locking) can also be chosen as the time, which is possible because, as is described above, locking also triggers the start of a freezing process. With the sensor 71b, which is attached, e.g., to one of the pneumatic cylinders 28 for activating the locking pins, a delay time of approx. 500 ms results, for example. In the block diagram, the sensors 71, 71a, 71b are shown as an example of any number of sensors that can be connected. Of course, rather than a sensor signal, it may be suitable to use the switching signal from an electrically actuated valve as input signal for actuating the trigger control system 7.

The sensor 71, optionally together with additional sensors, is connected to a trigger input for the programmable LED light source 73 via a connection distribution board 72, which is used for selecting one of the attached sensors. The light source 73 emits a light pulse, as described above, via a glass fiber light guide as soon as the trigger signal is activated. In this manner, a delay time and the duration of the light pulse can be freely adjusted in the programmable light source 73 by means of a computer 74, via a control interface, which in this case is a serial RS232 connection of a known type, for example. The delay time is used to decrease the amount of time between activation of the sensor and the start of the pressure and cooling processes, i.e., to any desired value of less than 30 or 500 ms, respectively.

The light source 73 may be realized preferably in the form of an LED having a high light intensity or a semiconductor laser. For example, the light source can be an LED light source of the type LZ1 (e.g., LZ1 00B200 for blue light, wavelength of 460 nm) obtained from LED Engin, Inc. (San Jose, Calif., USA). An example of a suitable programmable light source is the "Schott LLS" produced by Schott AG (Mainz, Germany). A light source of this type generates pulses at adjustable pulse rate and pulse width, high light intensity (up to 275 lm) and various wavelengths, is compatible with all conventional types of light fibers, and includes interfaces that enable programming and control via computer. The stated light sources can be selected and used for various types of light—in the exemplary embodiment blue, but also red, dark red (i.e., long-wave red), orange (short-wave red), yellow, green, short-wave blue, white, IR, UV, etc.; the transparent material of the cartridge 30 may optionally be suitably adjusted based upon the light that is used.

Thus, the entire sequence of preparing a sample applying freezing under high-pressure conditions according to the invention, in a typical example employing the exemplary embodiment is as follows:

positioning the sample in the support plate and assembling the cartridge;
    loading the cartridge into the holder;
    inserting the holder, along with the cartridge, into the high-pressure chamber, and locking the holder;
    performing cryopreservation following light stimulation;

releasing the pressure (via an outlet opening as described above, or by opening a release valve);

removing the cartridge and further preparing the sample (resting in the cartridge or removed therefrom).

In other embodiments, the individual steps may vary according to the selected application.

Actual cryopreservation following light stimulation comprises the steps of stimulating the sample with light through the viewing window, followed by high-pressure preservation of the sample by initiating the flow of cooling medium (LN2) into the chamber (e.g., by opening the intake valve). These two processes are initiated relative to one another according to a predefined time correlation.

In synchronizing the timing of these two events, including a predefinable time delay, it may be suitable to exploit the specific instrumental details of the high-pressure freezing system. For example, in the described embodiment, the above-mentioned fact may be utilized that a delay of fixed duration, which generally offers sufficient time for light stimulation, occurs between activation of the cooling medium system 8 (e.g., the opening of the intake valve 85) and the onset of the freezing process. Therefore, light stimulation is triggered by the stated activation of the cooling medium supply 8. This enables a sequence of the two events within a very short time interval of less than 500 ms.

Of course, multiple modifications and further developments of the specified invention are possible, without departing from the field of the invention, which is not limited to the described exemplary embodiment, and is instead defined by the claims. For example, any other known cryogen which is suitable for the respective application can also be used as a cryogenic liquid in place of LN2. Light stimulation can be implemented by irradiation with any type of desired light, monochromatic or with desired light spectra, wherein not only the visible range, but also IR and/or UV light can be used as necessary. Stimulative light may also be radiated directly from the light source (i.e., without use of a light guide), in which case the light source may be positioned directly at the opening of the window insert.

What is claimed is:

1. A device (1) for light stimulating an unfrozen aqueous sample (3) under normal pressure and freezing the aqueous sample (3) in a rapid manner avoiding formation of ice crystals in the sample, the device comprising:
    a high-pressure chamber (11) configured for insertion of a sample holder (30) containing the sample (3) and adapted to be sealed in a pressure-tight manner;
    a cooling medium supply adapted to feed a pressurized cooling medium into the high-pressure chamber (11) to the site of the sample holder (30) located therein;
    a light source (73);
    the high-pressure chamber (11) having a light passage ending in a window structure (2) including a pressure-tight window (20), the light passage being configured to direct light supplied from the light source (73) through the pressure-tight window (20) toward the sample (3) located in the sample holder (30);
    a control unit (74) connected to the light source (73), wherein the control unit is configured to set and control a duration of a pulse of light supplied from the light source (73) and a delay time between completion of the pulse and feeding the pressurized cooling medium; and
    the high-pressure chamber being impermeable to light except for light directed through said light passage.

2. The device according to claim 1, wherein the window (20) includes a window element made of a high-pressure-resistant material which is transparent to the light supplied to the high-pressure chamber from the outside, wherein the window element is held by a pressure- and temperature-resistant window bearing (22) provided in the high-pressure chamber (11).

3. The device according to claim 1, further comprising a sample holder (30) in the high-pressure chamber, wherein the sample holder (30) is at least partly made of a material transparent to the light supplied to the high-pressure chamber from the outside.

4. The device according to claim 3, wherein the sample holder (30) comprises a sample support (33) and at least one transparent shell piece (31, 32), wherein the sample support (33) has an opening (37) for receiving the sample (3) and the at least one shell piece (31, 32) has a channel for a cooling medium, wherein the sample support (33), when mounted in the sample holder (30), is enclosed by the at least one shell piece (31, 32), and the channel in the at least one shell piece leads from an external orifice to an area of the opening (37) in the sample support.

5. The device according to claim 1, wherein an output for a sensor or switching element (71, 71*a*) of a cooling medium circuit, which feeds the cooling medium into the chamber, can be connected to the control unit, and the light source (73) is configured to be activated at an adjustable time interval from a trigger signal supplied by the sensor.

6. The device according to claim 1, wherein the light passage is adapted to receive a light guide (23) inserted therein through which light supplied from the outside can be directed through the pressure-tight window (20) toward the sample (3) located in the sample holder (30).

7. The device according to claim 6, wherein the light guide (23) is configured to be inserted into the light passage into a position butting against the window (20).

8. The device according to claim 6, wherein the light source (73) is adapted to emit light into said light guide (23), and the light guide (23), when inserted into the light passage, has an axis aligned with a location of the sample (3).

* * * * *